United States Patent [19]

Kamen

[11] Patent Number: 4,673,820
[45] Date of Patent: Jun. 16, 1987

[54] DROP DETECTING SYSTEM WITH FOCUSING MIRROR ELEMENT AND VIBRATOR

[75] Inventor: Dean L. Kamen, Bedford, N.H.

[73] Assignee: Baxter Travenol Laboratories, Deerfield, Ill.

[21] Appl. No.: 669,108

[22] Filed: Nov. 7, 1984

[51] Int. Cl.⁴ ............................................. G01N 15/06
[52] U.S. Cl. ..................................... 250/573; 604/253
[58] Field of Search ............................... 604/251–255, 604/65; 250/573–577; 356/335–343, 441, 442, 246

[56] References Cited

U.S. PATENT DOCUMENTS 3,563,090 2/1971 Deltour ................................ 604/253
3,989,381 11/1976 Fulwyler ............................. 356/338
4,261,388 4/1981 Shelton ................................ 604/253
4,496,351 1/1985 Hillel et al. ......................... 604/253
4,533,350 8/1985 Danby et al. ....................... 604/253

Primary Examiner—David C. Nelms
Attorney, Agent, or Firm—Bromberg, Sunstein & McGregor

[57] ABSTRACT

An arrangement for improving the detection of drops in a drip chamber has a mirror element configured to focus light from a source to a detector in such a manner that a falling drop occludes a significant portion of the light reflected to the detector. In a preferred embodiment the mirror is located slightly below the drop forming orifice of the drip chamber and is shaped like an arcuate band of a curved surface. In a further preferred embodiment, a rotary motor with an eccentric weight is briefly energized to vibrationally clear any accumulation of droplets from the chamber wall. Other embodiments utilize a plurality of mirror elements to define an optical path from the source to detector which traverses the region throught which a drop falls 3 or more times.

12 Claims, 8 Drawing Figures

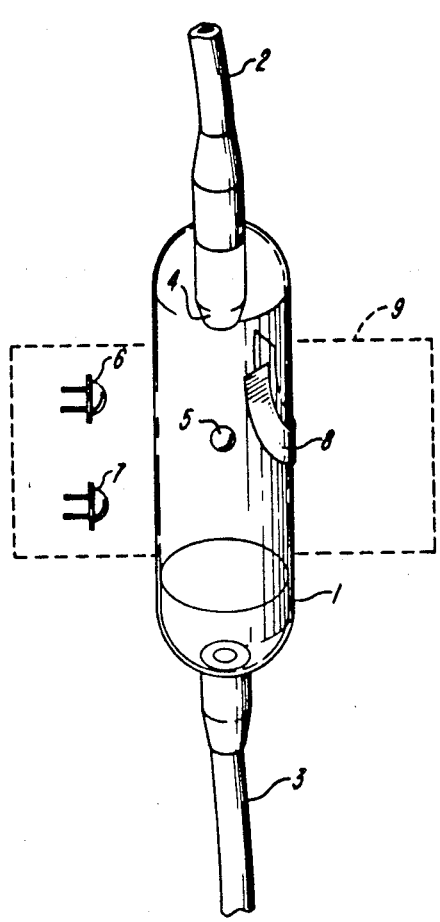
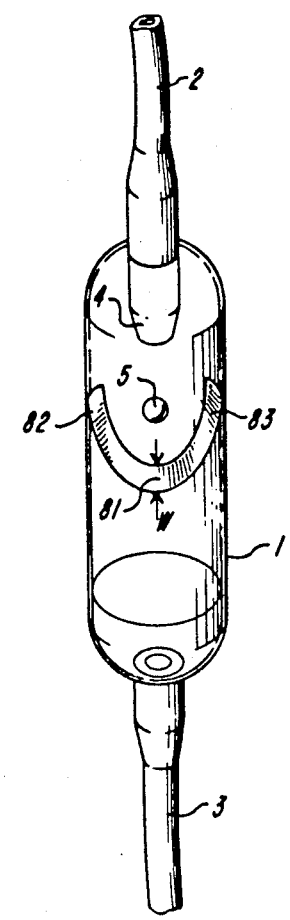
FIG. 1
FIG. 2
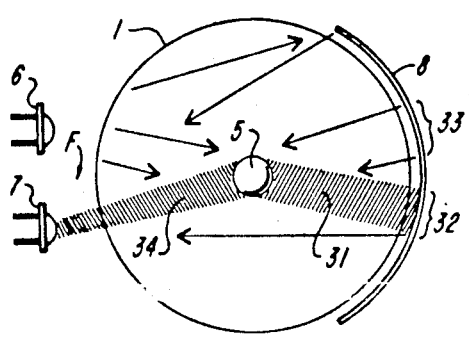
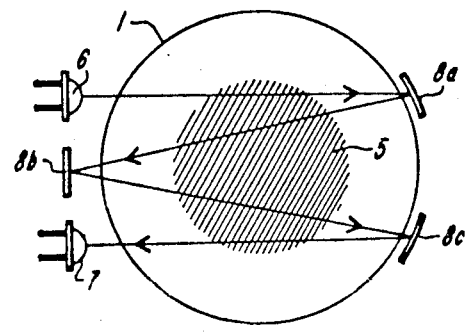
FIG. 3A
FIG. 3B

DROP DETECTING SYSTEM WITH FOCUSING MIRROR ELEMENT AND VIBRATOR

BACKGROUND OF THE INVENTION

The present invention relates to drop monitoring devices and in particular to such devices as used for counting drops of medicine or other infusion liquid in an intravenous delivery system, and operative to develop a signal upon the occurrence of a drop falling in a drip chamber in such a system.

Drop counting fluid delivery systems are known, and are in common use for delivery of all manner of infusions in a hospital or clinical setting. Such systems may be characterized in having a fluid reservoir, a drop forming chamber, and a fluid delivery tube extending, via a catheter, from the drop forming chamber into the vascular system of a patient. A drop sensor surrounds the drip chamber and senses the occurrence of a falling drop.

While several means of drop sensing are known, the prevalent mechanism is one in which a beam of light is directed across the drip chamber to a light detector, so that the beam is occluded each time a drop falls. Such systems, while of general practicality, have several inherent drawbacks. One is that because medical personnel prefer to visually confirm the operation of the system, the drip chambers are generally transparent, leading to a high level of ambient light. In such conditions, transient bursts of illumination, such as sunlight reflected from moving metallic objects, may operate to saturate the detector and blind it to an actually occurring drop, or may operate to trigger a false drop count. Solutions to this problem in the prior art involve elaborate signal averaging techniques, illumination stabilizing circuitry, and shielding of the portion of the drip chamber near to the detector/light elements. A further problem occurs in such systems because the trajectory of a falling drop follows a true vertical, whereas the drip chamber itself, being attached to an infusion tube, may be pulled at an angle off the vertical. The resulting effect is misalignment between the optimal path for drip detection and the actual drop path, leading to ambiguous or unreliable detection signals. Furthermore, because most infusion liquids are essentially transparent, the actual amount of light absorbed or scattered by a drop of such liquids may be a small percentage of the nominal light beam amplitude, so that signal discrimination is difficult, even in the absence of the other effects noted above.

The detection of drops can be frustrated by the accumulation of droplets on the wall of the drip chamber.

In such cases, a user flicks the chamber with his finger, causing a vibration to clear the accumulation from the wall.

One method known in the art for facilitating the counting of transparent liquid drops at low levels of general illumination is shown in U.S. Pat. No. 3,217,709 issued for an invention of J. H. Schneider et al. That patent shows a curved reflective clip which fits around a drip chamber and having a focus at the point of drop formation. The reflector is open on one side, so that when illuminated by the essentially parallel rays of a flashlight beam, all the incoming light is focussed upon the forming drop, causing it to appear bright. When the drop falls a sudden darkness is apparent. The device of that patent is configured for direct visual observation with both a light source and an observer far from the chamber, and is not adapted to an automated drip counting system. Also known in the art is the expedient of using a single mirror to reflect light across a drop path from a light source to a light detector in a photoelectrically operated drop counting apparatus. Such a configuration is shown in U.S. Pat. No. 3,563,090 issued for an invention of B. V. Deltour, at FIG. 4 thereof. The mirror in that device is apparently used simply to gain flexibility in the location of the various components (source, detector) within the drop detector housing; it does not show awareness of the signal enhancement possibilities using such a mirror.

SUMMARY OF THE INVENTION

In accordance with the present invention, an arrangement is provided for improving the detection of drops in a drip chamber. A mirror element is configured to focus light from a source to a detector in such a manner that a falling drop occludes a significant portion of the light reflected to the detector. In a preferred embodiment the mirror is located slightly below the drop forming orifice of the drip chamber and is shaped like an arcuate band of a spheroidal or other curved surface. The band is of a width corresponding to, and preferably slightly greater than, the width of a drop, and curves in an upward U-shape about the drop former, allowing close placement to the orifice while not permitting a drop to occlude the mirror until it has actually detached from the drop former. In a further preferred embodiment, the side portions of the band are flared wider than the central portion, so as to provide proportionately more light reflective area off axis than at the central portion. This increased reflectivity compensates for the angular drop off curves of source light intensity and of detector sensitivity, so that the occlusion of light by a falling drop results in a substantially uniform change in detector signal independently of the drip chamber axial orientation. In this embodiment, a rotary motor with an eccentric weight or other vibratory means is briefly energized to vibrationally induce clearing of accumulations from the drip chamber wall.

In a second embodiment, a plurality of mirror elements are placed so as to define an optical path from the source to detector which traverses the region through which a drop falls 3 or more times.

BRIEF DESCRIPTION OF THE DRAWINGS

These and other features of the invention will be appreciated by reference to the drawings, in which:

FIG. 1 shows functional elements of a drip chamber with drop monitoring system according to the present invention;

FIG. 2 shows a front view of the drip chamber with the drip forming tube, a falling drop and mirror according to the present invention;

FIG. 3A shows a schematic section through the chamber of FIG. 1 with a vertical projection of the mirror;

FIG. 3B shows a horizontal section of an alternative embodiment having plural mirrors;

DESCRIPTION OF THE INVENTION

Figure 4:
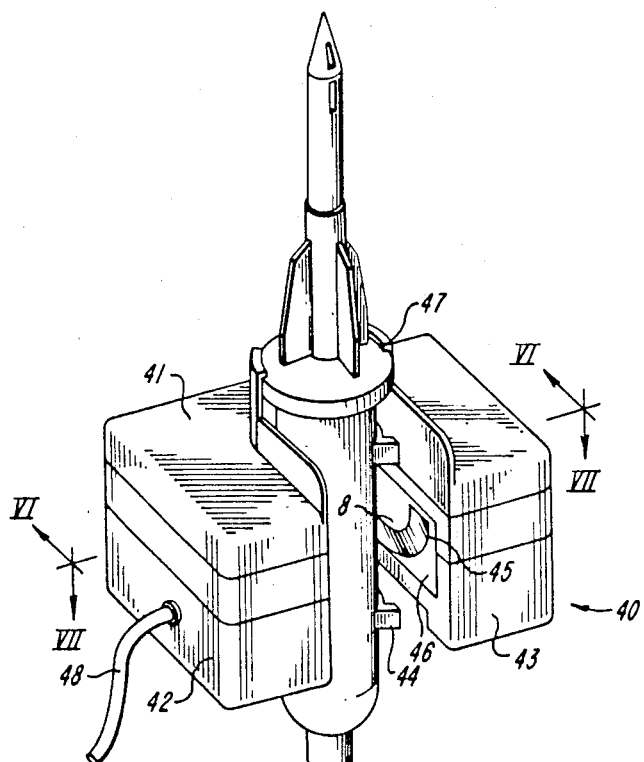
FIG. 4 shows a perspective view of a clip on monitor embodiment of the invention.

FIG. 1 shows a perspective view of a fluid drop monitoring system embodying the present invention. As shown, a medical fluid reservoir is connected via an inlet tube 2 to a drip chamber 1 having a drop former 4 operative to meter the fluid by drops into a lower pool whence the fluid flows, via outlet tube 3 to the patient. Along the path of a falling drop are disposed a light source 6 and a light detector 7 so placed that the drop causes a measurable disturbance in the characteristics of the detector as it passes by. Source 6 and detector 7 are physically housed in a housing, indicated conceptually by broken line 9, which serves to shield the light assembly and may also house signal processing circuitry.

According to the present invention, a reflective element or mirror 8 is placed in the optical path from the source to the detector to focus the source light onto the detector. The mirror curves around the drip chamber, and is configured to focally reflect light originating at source 6 to detector 7, along an optical path that includes one or more traverses of the region of the falling drop. In the embodiment shown, the source and detector are placed adjacent to each other around a central plane passing through the axis of the drip chamber and slightly beyond the focus of mirror 8. Because the mirror wraps around the chamber, the occlusion of the optical path caused by a falling drop is substantially independent of slight perturbations of the drop fall axis. Thus, even if the chamber is slanted e.g. 20 degrees from a vertical axis due to lateral pulling of its outlet tube 3, the drop will fall through a region whose light flux is focussed on the detector, and will be detected.

FIG. 2 shows further details of the design of mirror 8, which assure both that the occlusion by a falling drop is a substantial and measurable portion of the total light detected, and that the portion is relatively independent of chamber orientation or drop path. As shown, mirror 8 has approximately the shape of a narrow band of a width w approximately the diameter of a drop 5. Thus when a drop 5 is located between source 6 and mirror 8, its shadow will cover substantially the full width of the mirror, diminishing the light reflected to the detector. Center portion 81 of mirror 8 is of lesser width than lateral portions 82, 83, so that the lateral portions will focus the light flux striking a larger region of the mirror onto the detector. This configuration assures that, even though the light source 6 will generally have a light emission intensity distribution that drops off at the edges of its field of illumination, and the detector 7 will generally have a similar drop-off of sensitivity, the increased area contributing to the detected light at the edges will result in a substantially uniform amount of light blocked by a drop, whether the drop falls on-axis, or off to the side.

As shown in FIG. 2, in a preferred embodiment, mirror 8 is placed approximately just below the level of the drop forming orifice 4 of the drip chamber, and is of a generally U-shaped configuration with the central cutout portion of the U behind the region at which a drop forms. Thus, just after the drop detaches from the orifice, it will cross in front of the mirror. This configuration results in a slow drop velocity in front of the detector, and a substantially uniform occlusion of the mirror independently of perturbations of the drop axis, due, e.g., to a crooked chamber. Furthermore, because of its height, the mirror is not prone to splatter from the lower pool of fluid. By contrast with prior art drip detectors, in which an off-axis drop could hit the chamber wall before passing the light beam, and run down undetected, the present mirror device detects the drop as soon as it falls, even if it falls almost sideways directly to the chamber wall.

Shown in FIG. 3A is a schematic horizontal section of an embodiment of the present device, showing in schematic form the effect of a drop falling past the source, mirror and detector of the present invention. As shown, source 6 is located approximately in the focal region F of mirror 8. Light emitted from source 6 passes generally through chamber 1, strikes mirror 8 and is reflected back through the chamber to detector 7 which is also generally in the focal region F. (As used herein the term "focal region" is used to designate a diffuse region such that the light emitted from the source toward the mirror is focussed into approximately that region. The preferred embodiment of the invention uses a source and detector located slightly above and below the level of the mirror respectively, and in proximity to a single such region. However the term is intended to also encompass a focal region of a symmetrical or skewed mirror configured to focus the light from a particular source to a detector located in a distinct and different region, e.g. off to one side.) As shown in FIG. 3A, drop 5 casts a shadow 31, darkening portion 32 of mirror 8. Thus, in the presence of a drop, the light which would otherwise hit portion 32 does not get reflected to the detector. Similarly, a segment 33 of the mirror reflects light which, although focussed at the detector 7, hits drop 5 and is thus "eclipsed" by the drop, with a penumbra or shadow 34. Thus, in the presence of a drop, light reflected from mirror segment 33 also does not reach the detector. Thus the light from segments 32, 33 which together may comprise, for example, one-fifth or more of the arcuate length of mirror 8, is obscured by the drop, resulting in a substantial and dependably detectable change in the light flux focussed on the detector.

It will be recalled that the mirror 8 is a narrow band of a width corresponding to the drop dimensions, so that the foregoing discussion, although illustrated in cross-section and of a single dimension, substantially models the actual signal to noise enhancement of the present invention. It will be further appreciated that because the mirror is configured to focus light from the source to the detector, spurious light originating elsewhere will in general be focussed away from the detector, so that this source of noise is attenuated.

As shown in FIGS. 1–3A, mirror 8 surrounds a portion of the drip chamber. In a preferred embodiment, mirror 8 comprises a reflective band such as a tape or coating, adhered to or otherwise formed on the surface of the drip chamber itself.

FIG. 3B shows in horizontal section an alternative embodiment of the present invention, in which plural mirrors 8a, 8b, 8c etc. are positioned to serially reflect a beam of light from source 6 across the region of the drop fall path a plurality of times, ultimately to the detector 7. With this embodiment, not only does a drop falling somewhat outside its normal axis still occlude the beam, but, in general, a normally-positioned drop will simultaneously occlude the beam at several segments along the optical path, resulting in increased light absorbance and diffusion and a consequently better-defined signal generated by the detector The mirror segments 8a, 8b, etc. may each be planar, or they may be configured to focus the light reflected by them.

FIG. 4 shows the mirror of the present invention, in another embodiment, incorporated in a clip-on drop monitor 40. As shown, monitor 40 comprises a housing 41 having two opposing portions 42, 43 spaced apart and configured to fit around a drip chamber. Resilient clips 44 are positioned to receive the drip chamber and hold it centrally aligned between portions 42, 43. Housed in portion 42 are a light source 6 and detector 7 (not shown). Housed in portion 43 is mirror 8, which, as shown, is mounted on contoured mirror block 45. Block 45 is preferably a molded plastic block having a surface 46 on which a reflective tape or coating forming the mirror 8 is attached or formed. Surface 46 is configured to have the focal properties discussed in relation to FIGS. 1-3A above, with reference to the particular location and geometry of the source, detector, drop former and mirror. A slot 47 or other vertical registration means may be provided to assure the proper vertical registration of the drop former of a drip chamber within the housing at the level of mirror 8. Signal processing or power circuitry may also be mounted within the housing, and connected via cable 48 to a programmable control device.

Figure 5:
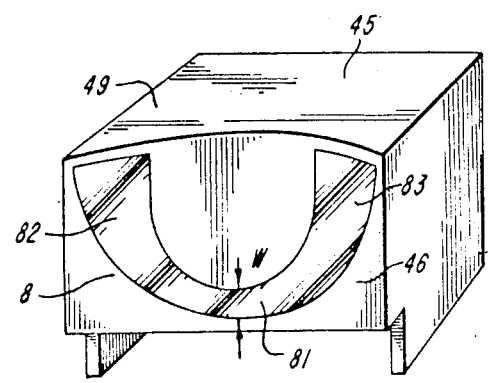
FIG. 5 shows a detail of the mirror block of the embodiment of FIG. 4.

FIG. 5 shows further details of the mirror block 45 of the embodiment of FIG. 4. As shown, the block 45 is a roughly rectangular block having a contoured front face 46 with mirror 8 formed or attached thereon. As in the previously discussed embodiment, mirror 8 has a central region 81 preferably of a width w not much larger than the nominal drop diameter, and flared end portions 82, 83 of somewhat greater width. As shown, contoured face 46 intersects the top face of mirror block 45 along edge 49, which is curved. Preferably face 46 is a portion of surface of revolution chosen so that mirror 8 will focus light at the appropriate region 42 of the monitor to strike the detector. Mirror block 45 may be hollow, in which case it may serve to house circuit elements for signal processing, or other devices, such as a drop buzzer, discussed below.

Figure 6:
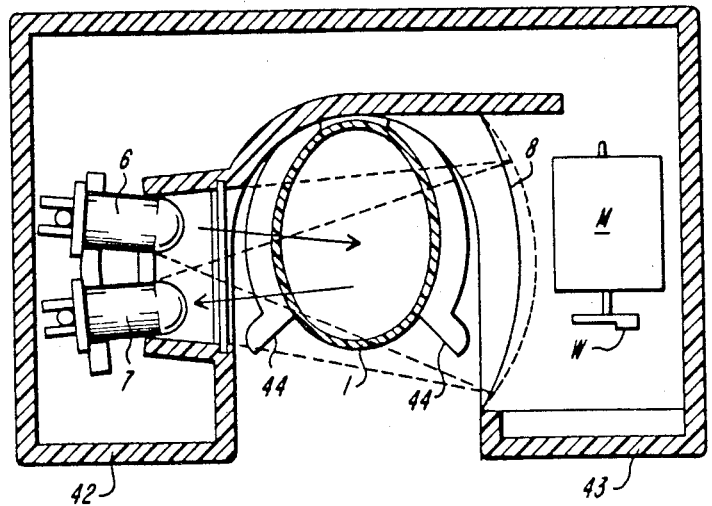
FIG. 6 shows a section along plane VI—VI of the embodiment of FIG. 4.

FIG. 6 shows a horizontal section along plane VI—VI of the monitor of FIG. 4, showing the placement of the light source 6 and detector 7 in portion 42, opposing the mirror 8 in portion 43. Also shown is a motor M having an eccentric or imbalanced wheel W mounted on its shaft, and placed in the hollow mirror block 45, previously described. Motor M is a miniature rotary electric motor, which because of its imbalanced wheel, is operative when energized to transmit a vigorous vibratory energy to the monitor assembly. Motor M is controlled by a microprocessor based controller to which the drop monitor assembly is attached, the controller being programmed so that upon the failure of the monitor to detect a drop for a predetermined time interval, motor M is energized for several seconds. In particular, whenever there has been detected a decrease in light level which lasts more than the usual duration of a drop, the situation may be caused by droplet accumulation, and the arrangement in a preferred embodiment is energized whenever this situation occurs. In another embodiment, the vibrator may run continuously. The rapidly rotating imbalanced wheel causes a strong vibration of the entire housing/drip chamber structure, thus clearing any accumulation of droplets from the wall of the drip chamber. Such an arrangement serves as a highly effective means for clearing the accumulation because of its efficient transfer of energy to the assembly. It thus replaces the manual finger-flicking commonly used for such purpose. The vibrating arrangement serves the further function of emitting an audible signal which may alert the user to possible line blockage or empty reservoir conditions.

Figure 7:
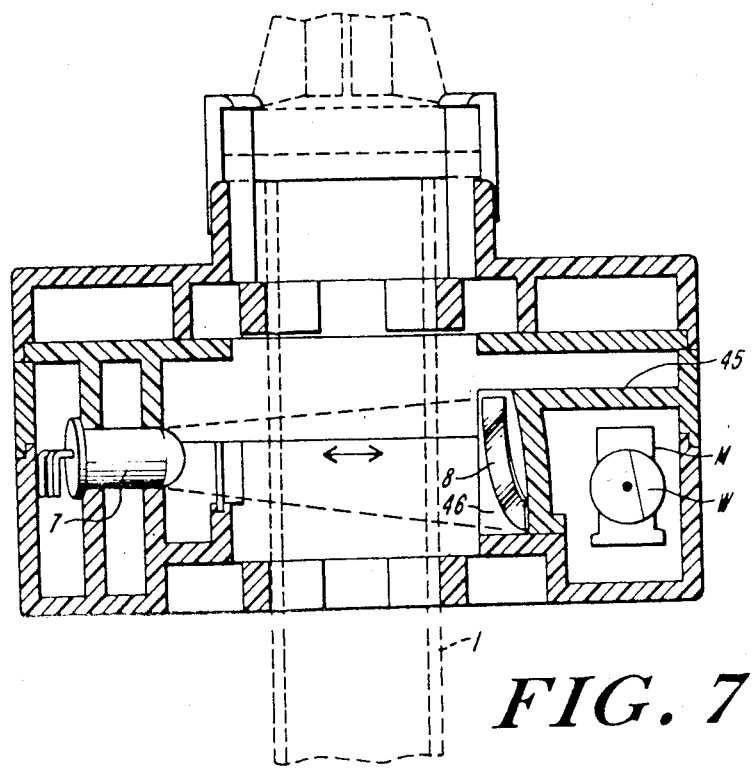
FIG. 7 shows a section along plane VII—VII of the embodiment of FIG. 4.

FIG. 7 shows a vertical section of the embodiment of FIG. 4, along the plane VII—VII. As shown, drip chamber 1 is held between the source/detector housing 42 and the mirror housing 43. Contoured face 46 of the mirror block is seen to have a curved vertical section, enabling mirror 8 to focus approximately in the region of detector 7. Mirror block 45 is seen to be hollow and to house motor M with eccentric weight W on its shaft.

The foregoing disclosure is by way of description only, and not limitation. Other variations of the invention will now occur to those skilled in the art, such as the expedient of forming a drip chamber in shape that includes a specially configured reflective region (i.e., a single reflecting element) or that has multiple reflective faces (analogous to FIG. 3B) for focusing a source light to a predetermined region outside the chamber. Additionally, the narrow band mirror (e.g. of FIG. 1) may be replaced by a separate external mirror for use with a drip chamber having a suitable mask (which may, for example, be painted on the chamber) defining a window of specified shape in communication with the mirror.

What is claimed is:

1. An improved drop monitoring system, of the type having a light source and a light detector with an optical path therebetween for detecting drops falling along a drop fall path across the optical path from the source to the detector, wherein the improvement comprises:
   a mirror element located in the optical path and configured so as to focus the source light onto the detector,
   the mirror element having a reflective surface in the shape of a band, the reflective band disposed transversely to the drop fall path and having a width, in a direction co-planar with the drop fall path, the width generally approximating the length of a falling drop, so that a falling drop occludes a substantial portion of the width of the band.

2. A system according to claim 1, wherein the band is a segment having end portions and a central portion, and the width is greater at the lateral portions than at the central portion, so as to reflect the light flux from a larger region at its ends than at its center.

3. A system according to claim 2, wherein the band is curved upward toward its ends so as to be of a generally U-shaped appearance with a central yoke portion and two arms, and is located so that the central yoke portion is vertically just below the beginning of the drop fall path, so that the optical path from the source to the detector via the mirror is occluded by a drop just after the drop commences to fall.

4. A system according to claim 1, wherein the mirror element is substantially symmetrically disposed around the nominal axis of the drop fall path and configured so that the detector is substantially uniformly sensitive to the falling of drops perturbed from such nominal axis by displacements occurring during normal use.

5. An improved drop monitoring system, of the type having a light source and a light detector with an optical path therebetween, for detecting drops falling along a drop fall path across the optical path from the source to the detector, wherein the improvement comprises:

a mirror element located in the optical path and configured so as to focus the source light onto the detector, the mirror element being affixed to a drip chamber and conformed with the surface thereof.

6. An improved drop monitoring system, of the type having a light source and a light detector with an optical path therebetween, for detecting drops falling along a drop fall path across the optical path from the source to the detector, wherein the improvement comprises:

a mirror element located in the optical path and configured so as to focus the source light onto the detector a housing including means for removably receiving a drip chamber, such housing containing the light source, light detector and mirror element, the housing further including vibratory means affixed thereto, for transmitting vibration to a drip chamber received therein and having an internal wall, to clear any accumulation of droplets from the wall.

7. An improved drip chamber of the type having a transparent wall and a drop forming means defining a drop path therein, for use in an optical drop monitoring system of the type having a light source and a detector for illuminating and detecting changes in the illumination of the region of the drop path of the chamber when a drop fills, wherein the improvement comprises:

a mirror element mounted on the chamber wall and configured to focus the illumination of a portion of the region of the drop path outside the chamber onto the light detector.

8. An improved drip chamber according to claim 7, wherein the mirror element is a U-shaped band centrally mounted on the chamber wall just below the level of the drop-forming means, so that the mirror focuses the illumination of the portion surrounding the drop just after the drop separates from the drop-forming means.

9. A drop monitoring system, such system comprising:

a housing defining a channel configured for receiving a drip chamber;

a light source located in the housing;

a light detector in optical communication with the light and located in the housing; and a mirror element substantially conformed in shape with the wall of the drip chamber, the mirror element being configured to focus onto the light detector, the light traversing a region that includes a section of the channel, such that a drop falling in the drip chamber passes through the region through which light is focused onto the detector.

10. A drop monitoring system according to claim 9, wherein the drip chamber includes an interior wall, the systeme further including vibratory means, located in the housing, for transmitting vibration to the drip chamber to clear any accumulation of droplets from the wall.

11. A drop monitoring system according to claim 10, wherein the vibratory means includes a rotary electric motor having an imbalanced weight on its rotor, such imbalance causing vibration when the motor rotates.

12. A drop monitoring system, such system comprising:

a housing defining a channel configured for receiving a drip chamber, such drip chamber having an interior wall;

a light source located in the housing;

a light detector in optical communication with the light source and located so that a drop falling in a received drip chamber will cause a signal indicative thereof to be generated by the detector; and vibratory means, affixed to the housing for vibrating the drip chamber to clear any accumulation of droplets from the wall.

* * * * *